United States Patent [19]

Simon et al.

[11] Patent Number: 5,137,709

[45] Date of Patent: Aug. 11, 1992

[54] LAYERED MIXED METAL HYDROXIDES FOR THE STABILIZATION OF RADIOACTIVE COLLOIDS

[75] Inventors: Jaime Simon, Angelton; David A. Wilson, Richwood; Kenneth McMillan, Richwood; Harrell L. Huff, Lake Jackson, all of Tex.

[73] Assignee: The Dow Chemical Company, Midland, Mich.

[21] Appl. No.: 656,397

[22] Filed: Feb. 15, 1991

[51] Int. Cl.$^5$ .............................................. A61K 43/00
[52] U.S. Cl. ..................................... 424/1.1; 252/625
[58] Field of Search .......................... 424/1.1; 252/625

[56] References Cited

U.S. PATENT DOCUMENTS

| | | | |
|---|---|---|---|
| 3,663,685 | 5/1972 | Evans | 424/1 |
| 4,752,464 | 6/1988 | Lieberman et al. | 424/1.1 |
| 4,758,429 | 7/1988 | Gordon | 424/85 |
| 4,790,954 | 12/1988 | Burba et al. | 252/315.5 |
| 4,849,209 | 7/1989 | Lieberman et al. | 424/1.1 |
| 4,889,707 | 12/1989 | Day et al. | 424/1.1 |
| 4,897,254 | 1/1990 | Simon et al. | 424/1.1 |
| 4,898,724 | 2/1990 | Simon et al. | 424/1.1 |
| 4,906,450 | 3/1990 | Lieberman et al. | 424/1.1 |
| 4,915,932 | 4/1990 | McLaren et al. | 424/1.1 |
| 4,970,062 | 11/1990 | Atcher et al. | 424/1.1 |
| 5,026,538 | 6/1991 | Lieberman et al. | 424/1.1 |
| 5,061,475 | 10/1991 | Lieberman et al. | 424/1.1 |
| 5,061,476 | 10/1991 | Lieberman . | |

OTHER PUBLICATIONS

C. B. Sledge et al., "Experimental Radiation Synovectomy by 165 Dy Ferric Hydroxide Macroaggregate", *Arthritis and Rheumatism*, 20, pp. 1334-1342.
C. B. Sledge et al., "Intra-articular Radiation Synovectomy", *Clinical Orthopedics and Related Research*, 182, pp. 37-40 (1984).
C. B. Sledge et al., "Treatment of Rheumatoid Synovitis of the Knee with Intra-articular . . . "*Arthritis and Rheumatism*, 29, pp. 153-159 (1986).
L. K. Doepel, "Radionuclide Therapy for Arthritic Knees", *J.A.M.A.*, 253, pp. 744-745 (1985).
P. F. M. J. Spooren et al., "Synovectomy of the Knee with 90 Y", *Nuclear Medicine*, pp. 441-445, (1985).
L. Rosenthall, "Use of Radiocolloids for Intra-articular Therapy for Synovitis", *Therapy in Nuclear Medicine*, pp. 147-242 (1978).
D. J. Hnatowich et al., "Dysprosium-165 Ferric Hydroxide Macroaggregates for Radiation Synovectomy", *J. Nuclear Medicine*, 19, pp. 303-308.
U.S. application Ser. No. 07/458,049, filed Dec. 27, 1989.

*Primary Examiner*—John S. Maples

[57] ABSTRACT

A stabilized radionuclide-colloid composition useful in therapeutic radiation ablation therapies is disclosed. The composition contains a viscosity modifier layered mixed metal hydroxide and optionally an ion exchange medium to stabilize the radioactive colloid.

34 Claims, No Drawings

LAYERED MIXED METAL HYDROXIDES FOR THE STABILIZATION OF RADIOACTIVE COLLOIDS

FIELD OF THE INVENTION

This invention relates to a composition, a method of making the composition, and a method of using the composition in treating arthritis and other diseases where a radioactive colloid is used in therapeutic and diagnostic procedures. In particular, the composition of this invention comprises a radioactive colloid having admixed therewith a stabilizing effective amount of a layered mixed metal hydroxide. The composition exhibits increased retention of radioactivity at a site of injection, for example, in a synovium, as compared with the retention of formulations without such a stabilizer.

BACKGROUND OF THE INVENTION

Rheumatoid arthritis is a prevalent disease characterized by chronic inflammation of the synovial membrane lining the afflicted joint. Current treatment methods for severe cases of rheumatoid arthritis include the removal of the synovial membrane, e.g., synovectomy. Surgical synovectomy has many limitations, including the risk of the surgical procedure itself, and the fact that a surgeon often cannot remove all of the diseased membrane. The diseased tissue remaining eventually regenerates, causing the same symptoms which the surgery was meant to alleviate.

Radiation synovectomy is radiation-induced ablation of diseased synovial membrane tissue accomplished by injecting a radioactive compound into the diseased synovium. Early attempts to perform radiation synovectomy were hampered by migration of the radioactive compounds utilized and by leakage of such compounds from the synovium and into surrounding healthy tissues. The instability of labile radionuclide-complexes or the presence of small labeled particles resulted in radionuclide leakage out of the synovium and deposition in healthy tissues. Significant leakage of the radioactive compound from the injection site exposed normal tissues to dangerous levels of radiation. Because of these limitations, new radiolabeled compounds were sought which would have minimal leakage.

U.S. Pat. No. 4,752,464 describes a composition comprising a radioactive colloid in which a radionuclide is entrapped within an iron hydroxide matrix. Radioactive colloids are useful in radiation ablation procedures, for example, ablation of a synovium in rheumatoid arthritis, however their use may still result in significant leakage of radioactivity from a site of injection, e.g., a synovium, and into the surrounding normal tissues, exposing normal tissues to an undesirable amount of radiation. To compensate for the leakage, a radioactive metal having a short half-life, such as Dysprosium (Dy-165) has been proposed for use as the labeling radionuclide. Because of its short half-life (2.3 hours), the majority of Dy-165 radioactivity decays before significant leakage can occur, thereby minimizing the dose of radiation seen by normal tissues.

The use of radioactive metals having a short half-life severely limits the utility of the therapeutic radiation procedure in two ways. First, radioactive compositions prepared with short half-life isotopes lose a significant amount of radioactivity because of decay during shipment to distant locations. Second, to achieve a therapeutic dose of a composition comprising a radioactive metal having a short half-life, large amounts of radioactive materials must be used. As a result, clinical personnel must handle large amounts of radioactive materials.

There remains a need for a therapeutic radioactive composition which upon injection, for example, into a synovium, would remain at the site of injection, e.g., within a synovium, for a prolonged period of time. Prolonged retention at the site of injection would allow use of radionuclides having a longer half-life in therapeutic procedures, including radiation synovectomy, without fear of significant leakage from the site of injection and radiation exposure to normal tissues.

SUMMARY OF THE INVENTION

It has now been found that the addition of a layered mixed metal hydroxide (LMMH) to a radiolabeled colloid composition results in a stabilized radiolabeled colloid composition. Use of the stabilized colloid-LMMH compositions in therapeutic procedures results in significantly reduced leakage of radioactivity from a site of injection, for example, a synovium. The stabilized colloidal compositions contain a radionuclide, a colloid, and a LMMH. The colloid may be a metal hydroxide colloid such as iron (II or III) hydroxide or a colloidal clay such as bentonite. The stabilized colloidal compositions may be prepared using radionuclides having longer half-lives than previously used, greatly minimizing significant leakage from the site of injection and radiation exposure to normal tissues.

DETAILED DESCRIPTION OF THE INVENTION

In the method of the present invention a radioactive colloid is stabilized by the addition of a layered mixed metal hydroxide (LMMH). Such stabilized radioactive colloids are useful in the therapeutic radiation treatment of arthritis to ablate diseased tissues.

Stabilization of radioactive colloids includes the prevention of leakage of radioactive nuclides from a site of injection into surrounding normal tissues. The stabilized compositions of the present invention contain therapeutic radionuclides, radionuclide-absorbing colloids, and stabilizing LMMHs.

While not wishing to be bound by theory, the addition of LMMH to the radioactive colloid composition may achieve stabilization by increasing the viscosity of the composition.

PREPARATION OF COMPONENTS OF THE STABILIZED PRODUCT

Colloids

Colloidal materials useful in the present invention include any which are capable of being labeled with a therapeutically useful radionuclide. The term colloid is meant to include both the material in the dispersed phase and the dispersion medium comprising the colloidal system. The dispersion medium may be liquid or gaseous, and preferably is liquid. Useful colloids are anionic colloidal materials, including, but not limited to, metal hydroxide colloids such as iron hydroxide colloid, colloidal clays such as bentonite, macroaggregated protein such as macroaggregated albumin, ion exchange gels or resins, and polyamines. The preferred metal hydroxides are iron hydroxide, including iron (II) hydroxide and iron (III) hydroxide, and aluminum hydroxide.

Bentonite, a colloidal clay primarily composed of montmorillonite ($Al_2O_3.4SiO_2.H_2O$), may bind radioactive metals by entrapment in the highly viscous colloidal matrix, or by ion exchange.

Radionuclides

Radionuclides useful in the present invention include those having therapeutic efficacy, for example in radiation ablation therapies such as radiation synovectomy. Radionuclides are preferably those of the rare earth class and other metals having nuclear properties of therapeutic value. Examples of such metals include Holmium (Ho-166), Samarium (Sm-153), Lutetium (Lu-177), Lanthanum (La-140), Gadolinium (Gd-159), Ytterbium (Yb-175), Indium (In-115), Yttrium (Y-90), Scandium (Sc-47), and Rhenium (Re-186), (Re-188).

The respective radionuclides can be produced in several ways. In a nuclear reactor, a nuclide is bombarded with neutrons to obtain a nuclide with additional neutrons in its nucleus. For example:

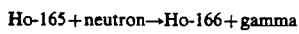

Typically, the desired radionuclide can be prepared by irradiating an appropriate target, such as the metal oxide. Another method of obtaining radionuclides is by bombarding nuclides with particles in a linear accelerator or cyclotron. Yet another way of obtaining radionuclides is to isolate them from fission product mixtures. Radionuclides may be obtained by methods known in the art.

Preparation of Radioactive Colloid

Labeling of the colloid may be accomplished by ion exchange, sorption, entrapment, or other known methods for bonding a radionuclide to an anionic colloid.

Radiolabeled metal hydroxide colloids useful in the method of the present invention include those produced by a coprecipitation method as described in U.S. Pat. No. 4,752,464, which is hereby incorporated in full for reference. Preferably, the product of coprecipitation process includes particles in the size range of 3–20 μm.

Useful radiolabeled metal hydroxide colloids may also be produced by sorption of a radionuclide onto a previously prepared metal hydroxide colloid. In this procedure, a metal hydroxide colloid may first be prepared, for example, by reacting a metal salt with sodium hydroxide. The resultant metal hydroxide colloid is then reacted with nuclide to produce the radioactive colloid.

Layered Mixed Metal Hydroxides (LMMH)

LMMH may be represented by the following formula:

where:
m represents the number of Li ions present;
D represents divalent metal ions;
d is the number of ions of D in the formula;
T represents trivalent metal ions;
A represents monovalent or polyvalent anions other than OH ion;
a is the number of ions of A in the formula;
n is the valence of A; and
(m+2d+3+na) is equal to or greater than 3.

Layered mixed metal hydroxides are preferably prepared by an instantaneous ("flash") coprecipitation wherein soluble metal compounds, e.g. salts of the metals are intimately mixed (using non-shearing agitation or mixing) with an appropriate alkaline material which supplies hydroxyl groups to form the mixed metal hydroxide crystals. A distinguishing feature of the composition is that the crystals are essentially a monolayer, that is, one layer of the mixed metal hydroxide per unit cell of the crystal. These are termed "monodispersed" crystals when they are in a liquid carrier and are individual crystals of monolayer mixed metal hydroxides. (See EPO No. 0,207,811, U.S. Pat. Nos. 4,664,843 and 4,790,954.)

In the above formula I, m may be from 0 to about 1, and most preferably m is 0.5 to about 0.75 when not 0. The D metal may be Mg, Ca, Ba, Sr, Mn, Fe, Co, Ni, Cu, Zn, and most preferably D is Mg, Ca, or mixtures of these. The value of d may be from 0 to about 4, provided that both m and d are not 0, and preferably the value of d is from about 1 to about 3 and most preferably about 1. The T metal is preferably trivalent, and may be Al, Ga, Cr, or Fe; preferably T is Al or Fe, and most preferably T is Al. The A anions may be monovalent or polyvalent, including divalent and trivalent, and they may be inorganic ions such as halide, sulfate, nitrate, phosphate, carbonate. Preferably the A anions are halide, sulfate, phosphate or carbonate or they may be hydrophilic organic ions such as glycolate, lignosulfonate, polycarboxylate or polyacrylate. These anions often are the same as the anions which form part of the metal compound precursors from which these crystals are formed. Since "n" is a negative number, "na" is also a negative number.

Methods for preparing a LMMH useful in the present invention, are disclosed in U.S. Pat. No. 4,790,945 to Burba et al., which is incorporated in full by reference. To produce LMMH, according to the Burba et al. method, a mixture of the selected soluble metal compounds, especially the acid salts (e.g. chloride, nitrate, sulfate, phosphate, etc.) are dissolved in an aqueous carrier. The ratios of the metal ions in the solution are predetermined to give the ratios desired in the final product. The concentration limit of the metal compounds in the solution is governed in part by the saturation concentration of the least soluble of the metal compounds in the solution. Any non-dissolved portion of the metal compounds may remain in the final product as a separate phase. This is usually not a serious problem if the concentration of such separate phase is a relatively low amount in comparison to the soluble portions, and preferably is not more than about 20 percent of the amount of the soluble portions. The solution is then mixed rapidly and intimately with an alkaline source of $OH^-$ ions while substantially avoiding shearing agitation thereby forming monodispersed crystals of LMMH. One convenient way of achieving such mixing is by flowing the diverse feed streams into a mixing tee from which the mixture flows, carrying the reaction product, including the monodispersed LMMHs of the above formula I. The mixture may then be filtered, washed with fresh water to remove extraneous soluble ions (such as $Na^+$, $NH^{+4}$ ions, and other soluble ions) which are not part of the desired product.

A preferred method of preparing the formula I LMMH composition, is to react a solution of metal salts, preferably magnesium and aluminum salts (approximately 0.25 molar) with an appropriate base such as ammonium or sodium hydroxide in quantities sufficient to precipitate the LMMH. For ammonium hydroxide, the preferable range is between about 1 and about 1.5 equivalents of OH⁻ per equivalent of anion.

The precipitation should be done with little or no shear so that the resultant flock is not destroyed. One method of accomplishing this is to flow two streams, the salt stream and the base stream, against one another so that they impinge in a low shear converging zone such as would be found in a mixing tee. The reaction product is then filtered and washed, producing a filter cake of about 10% solids. (See European Patent Application No. 02 07 811)

The LMMH crystals have a positive charge associated with the surface of the LMMH crystals, and are consequently less readily dispersed in non-polar than in polar fluids. It may be desirable to modify the LMMH to render it more readily dispersed in the fluid of choice. Such modification may be accomplished, for example, by treating the LMMH crystals, for example, with an aliphatic carboxylic or fatty acid, such as stearic acid.

Ion Exchange Medium

In addition, the stabilized radioactive colloid composition may also include an anionic exchange medium to bind up excess nuclide in the radioactive composition. The ion exchange medium may also bind up radionuclides which become displaced from colloid at the site of injection, and help to prevent leakage of radioactivity from a site of injection. Ion exchange media useful in the present invention include negatively charged clays, for example, betonite, or other well known commercially available anionic exchange media.

PREPARATION OF THE STABILIZED PRODUCT

Stabilized Radioactive Colloids

The stabilized radiolabeled colloids of the present invention are generally prepared by mixing a colloid with a LMMH. The colloid may be radiolabeled prior to or simultaneously with the LMMH mixing step. In general, the colloidal material will be in suspension or solution. The LMMH may be in solid form, or in suspension. The amount of LMMH in the final colloidal composition will vary with the intended use, and will be that amount which is effective in reducing leakage of radioactivity from a site of injection of the composition. Generally, the amount of LMMH in the final composition will be in the range of from about 0.01 wt. % to about 2.5 wt. % of the total composition.

The LMMH is mixed with a colloid which carries the radionuclide, including, but not limited to iron hydroxide or negatively charged clays such as bentonite. The amount of the colloid in the final composition will vary according to the type of colloid and with the specific intended use of the composition, but generally will be in the range of about 0.5 wt. % to about 2.5 wt. % of the total composition.

In addition, an ion exchange medium may be added to the stabilized radioactive colloid composition to bind up excess radionuclide. The ion exchange medium may be a negatively charged clay such as betonite. Generally, the amount of ion exchange medium in the composition will be approximately less than 1.0 wt. % of the total composition.

The stabilized radiolabeled colloidal compositions of the present invention are useful in therapeutic and diagnostic procedures, and are particularly useful in the therapeutic radiation treatments for arthritis. These compositions are especially useful in therapeutic radiation ablation procedures, for example, radiation synovectomy. In such procedures, a therapeutically effective amount of the radioactive composition is administered to a patient in need of such treatment, for example, by injection into the synovium of an arthritic knee.

The therapeutically effective amount will vary with many factors including the half-life of the radionuclide utilized, the particular colloid used, the site of injection, and the desired amount of radioactivity to be delivered to the site of injection. Depending upon the therapeutic procedure, the desired amount of radioactivity delivered to the site of injection is that amount sufficient to kill or ablate the diseased tissue or cells. In general, this will be a sufficient amount of radioactive material to deliver from about 500 to about 150,000 rads to the diseased tissue. A more preferred dosage is that which delivers form about 2,000 to about 50,000 rads to the diseased tissue.

The invention will be further clarified by consideration of the following examples, which are intended to be purely exemplary of the method of the invention.

EXAMPLES

Example 1

Preparation of LMMH, $MgAl(OH)_{4.7}Cl_{0.3}$

LMMH was prepared according to the method of Burba, disclosed in U.S. Pat. No. 4,790,954 which is hereby incorporated by reference. In general, a solution of $MgCl_2 \cdot AlCl_3$ (each 0.25M) was pumped into one arm of a mixing tee. $NH_4OH$ was pumped into a second, opposite arm of the tee so that the two solutions met in the tee. The coprecipitation product was poured out of the third arm and into a beaker, and consisted essentially of delicate flocs of monospheres, monolayer, and microcrystals of LMMH, having the approximate formula $MgAl(OH)_{4.7}Cl_{0.3}$ suspended in an aqueous solution of $NH_4Cl$. The product was filtered, washed and drain-dried, although the tiny LMMH crystals still contain water.

Example 2

Stabilization of Ho-166-Iron Hydroxide Colloid with LMMH

A volume of 15 ml of 0.01M $FeSO_4$ solution was placed in each of 4 vials and 15 ml of 0.1N NaOH was added to each vial. This was mixed and allowed to stand for 10 minutes. The vials were centrifuged for 2-3 minutes and the liquid fraction was removed by decanting. The solids were washed with 15 ml of water and the suspension was again centrifuged and decanted. Fifteen ml of phosphate buffer (0.4M, pH 7) was added and the solids were isolated by centrifugation followed by decanting. The solids were resuspended in 5 ml of phosphate buffer and combined into one 20 ml vial. After centrifuging the liquid was again removed by decanting. The solids were resuspended in 5 ml of Ho-166 solution ($3 \times 10^{-4}$M Ho in 0.1N HCl containing tracer amounts of Ho-166) and an additional 5 ml of water. The suspension was adjusted to a pH of approximately 7-8 using HCl.

To a vial containing the Ho-166-colloid was added 5.0 ml of $MgAl(OH)_{4.7}Cl_{0.3}$ (11.8% by weight in distilled water) as prepared in Example 1 and the suspension was mixed to suspend the colloids in the LMMH medium. After mixing, the composition was viscous.

A volume of 100 μl of this suspension was injected into the synovium in the stifle of an anesthetized rabbit. A 2 inch NaI detector connected to a multichannel analyzer was used to determine the amount of Ho-166 activity in the synovium as a function of time by counting the gamma photons using repeated one minute counts. No loss of activity from the synovium was detected for the time period studied, one hour. A control formulation lacking LMMH was tested in the rabbit's opposite stifle. A measurable loss of activity (approximately 2%) from the control synovium was detected for the one hour test period.

Example 3

Stabilization of Sm-153-Iron Hydroxide Colloid by LMMH

A mass of 0.203 g of $FeSO_4 \cdot 7H_2O$ was dissolved in 100 ml of deionized water. A volume of 4 ml of this 0.2% $FeSO_4$ solution was placed in a vial and 800 μl of 1.0N NaOH was added. The dark green solid that was formed was allowed to settle to the bottom of the vial and the excess liquid was decanted. The solid was washed four times by resuspending in 4 ml of deionized water, centrifuging at 4500 RPM for 1 to 2 minutes, and decanting.

A volume of 50 μl of Sm-153 solution ($3 \times 10^{-4}$ molar Sm, in 0.1N HCl containing tracer amounts of Sm-153) was added to the prepared colloid. LMMH, prepared as described for Example 1, was diluted in water to provide a LMMH dispersion of 11.8 wt. %. One ml of the LMMH dispersion was added to the Sm-153-colloid mixture, mixed and the pH adjusted to approximately 8-9 with HCl.

A volume of 100 μl of the resulting Sm-153-iron hydroxide-LMMH dispersion was injected into the synovium in the stifle of an anesthetized rabbit. The Sm-153 activity in the synovium was determined over time by placing a NaI scintillation detector over the knee area and counting the gamma photons using repeated one minute counts. The number of counts remaining in the synovium (corrected for decay) was then plotted as a function of time. The results showed no measurable loss of activity from the synovium over 120 minutes.

Example 4

Stabilization of a Sm-153 Iron Hydroxide Colloid with LMMH and Bentonite

Into a vial was placed 2 ml of 0.2% $FeSO_4$ (wt/vol). To this was added, dropwise, approximately 4 ml of 0.1N NaOH. A dark green solid was allowed to settle in the bottom of the vial and the supernatant was removed. The solid was resuspended in 4 ml of distilled water. The dispersion was then centrifuged at 4500 RPM for 3 minutes and the resulting supernatant removed. This distilled water washing step was repeated two additional times. After the last decanting of the supernatant, 200 μl of Sm solution ($3 \times 10^{-4}$ molar Sm in 0.1N HCl containing tracer amounts of Sm-153) was added, followed by the addition of 200 μl of isotonic saline.

A volume of 300 μl of a LMMH dispersion containing 1.4% Bentonite (Gold Star ®) and 0.21% LMMH (prepared as described in Example 1 and diluted in deionized water) was then added. After mixing, the dispersion was allowed to stand for 10 minutes, after which time 10 μl of 0.1 NaOH was added followed by an additional 300 μl of the LMMH-Bentonite dispersion.

A laboratory rabbit was anesthetized and 300 μl of the prepared radiolabeled colloid-LMMH-Bentonite dispersion was injected into the synovium of the right knee. The Sm-153 activity in the synovium was determined over time by placing a NaI scintillation detector over the knee area and counting the gamma photons using repeated one minute counts. The number of counts remaining in the synovium (corrected for decay) was then plotted as a function of time. No leakage of radioactivity from the synovium was detected over the 2.5 hours duration of the experiment.

Control

The procedure was repeated using 300 μl of the radiolabeled colloid to which no LMMH-Bentonite had been added. The same rabbit was injected with this control dispersion in the left knee synovium. The amount of activity remaining in the synovium was determined in the same manner as described above. In the control, left knee, a decrease in the amount of activity remaining in the synovium was evident by a decrease in the counts in the synovium with time.

Example 5

Stabilization of Sm-153-Bentonite with LMMH

A volume of 500 μl of LMMH-Bentonite dispersion containing 1.4% Bentonite and 0.21% LMMH (prepared as described for Example 1 and diluted in deionized water) was placed in a vial. Ten (10) μl of Sm solution ($3 \times 10^{-4}$ molar Sm, in 0.1 NHCl containing tracer amounts of Sm-153) was added. A volume of 100 μl of the resulting Sm-153-LMMH-bentonite dispersion was injected into the right knee synovium of an anesthetized rabbit. The amount of activity in the synovium as a function of time was determined and calculated as described in Example 1. Material prepared in the same manner was also injected into the left knee synovium of the rabbit. The number of counts in the synovium as a function of time remained constant for both samples.

Having described the invention above, various modifications of the techniques, procedures, material and equipment will be apparent to those in the art. It is intended that all such variations within the scope and spirit of the appended claims be embraced thereby.

What is claimed is:

1. A composition comprising:
   a colloid capable of being labeled with a radionuclide;
   a radionuclide; and
   a layered mixed metal hydroxide having the formula:

$$Li_m D_d T(OH)_{(m+2d+3+na)} A_a^n$$

wherein:

m is 0 to about 1;

D is a divalent metal ion selected from the group consisting of magnesium, calcium, barium, strontium, manganese, iron, cobalt, nickel, copper, and zinc or a mixture thereof;

d is 0 to about 4;

provided that both m and d are not 0;

T is a metal ion selected from the group consisting of aluminum, gallium, chromium, and iron;

A is a monovalent or polyvalent ion other than a hydroxyl ion;

n is the valence of the anion A;

a is the number of anions A in the formula;

$(m+2d+3+na)$ and is equal to or greater than 3.

2. The composition of claim 1 wherein said colloid is bentonite.

3. The composition of claim 1 wherein m is zero.

4. The composition of claim 1 wherein m is approximately 0.5 to approximately 0.75.

5. The composition of claim 1 wherein D is magnesium, calcium, or mixtures thereof.

6. The composition of claim 1 wherein d is approximately 1 to approximately 3.

7. The composition of claim 1 wherein T is aluminum or iron.

8. The composition of claim 1 wherein d is 1.

9. The composition of claim 8 wherein T is aluminum.

10. The composition of claim 1 wherein the radionuclide is a radioactive metal.

11. The composition of claim 10 wherein the radionuclide is Sm-153, Ho-166, Lu-177, La-140, Gd-159, Yb-175, In-115m, Y-90, Sc-47, Re-186, or Re-188.

12. The composition of claim 1 wherein said colloid is a metal hydroxide.

13. The composition of claim 12 wherein said metal hydroxide is iron hydroxide.

14. The composition of claim 13 wherein said iron hydroxide is iron (II) hydroxide.

15. The composition of claim 13 wherein said iron hydroxide is iron (III) hydroxide.

16. The composition of claim 1 further comprising an ion exchange medium.

17. The composition of claim 16 wherein the ion exchange medium is a negatively charged clay.

18. The composition of claim 17 wherein the negatively charged clay is bentonite.

19. The composition of claim 1 wherein m is 0, D is magnesium, and T is aluminum.

20. The composition of claim 19 wherein said layered mixed metal hydroxide has the formula:

$$Mg_xAl_y(OH)_zA_a^n$$

wherein:
x is approximately 1 to approximately 3;
y is approximately 1;
z is approximately 3 to approximately 5;
A is a halide, sulfate, phosphate, or carbonate;
n is the valence of A; and
a is approximately 0.1 to 1.0.

21. The composition of claim 20 wherein x is 1, y is 1, z is 4.7, and a is 0.3.

22. The composition of claim 21 wherein the radionuclide is Sm-153 or Ho-166.

23. A therapeutic radiation ablation treatment method comprising:
injecting into a synovium of a subject in need of such treatment a therapeutically effective amount of a stabilized radioactive colloid composition wherein the radioactive colloid composition contains a layered mixed metal hydroxide; wherein the layered mixed metal hydroxide has the formula:

$$Li_mD_dT(OH)_{(m+2d+3+na)}A_a^n$$

wherein:
m is in the range of 0 to approximately 1;
D is a divalent metal ion selected from the group consisting of magnesium, calcium, barium, strontium, manganese, iron, cobalt, nickel, copper, and zinc or a mixture thereof;
d is 0 to about 4;
provided that m and d are not both 0;
T is a metal ion selected from the group consisting of aluminum, gallium, chromium, and iron;
A is a monovalent or polyvalent ion other than an hydroxyl ion;
n is the valence of the anion A;
a is the number of anions A in the formula; and $(m+2d+3+na)$ is equal to or greater than 3.

24. The method of claim 23 wherein:
m is in the range of approximately 0.5 to 0.75;
D is Mg, Ca, or a mixture thereof;
d is in the range of approximately 1 to 3; and
T is a halide, sulfate, or phosphate.

25. The method of claim 23 wherein said administering is to a patient suffering from arthritis.

26. The method of claim 25 wherein said arthritis is rheumatoid arthritis.

27. The method of claim 23 wherein said radioactive colloid composition further contains a negatively charged clay.

28. The method of claim 27 wherein said clay is bentonite.

29. The method of claim 23 wherein said layered mixed metal hydroxide has the formula:

$$Mg_xAl_y(OH)_zA_a^n$$

wherein:
x is approximately 1 to approximately 3;
y is approximately 1;
z is approximately 3 to approximately 5;
A is a halide, sulfate, phosphate, or carbonate;
n is the valence of A; and
a is approximately 0.1 to 1.0.

30. The method of claim 29 wherein x is 1, y is 1, z is 4.7, and a is 0.3.

31. The method of claim 23 wherein said administering is of a radioactive colloid composition which contains a radioactive metal.

32. The method of claim 31 wherein the radioactive metal is Sm-153, Ho-166, Lu-177, La-140, Gd-159, Yb-174, In-115m, Y-90, Sc-47, Re-186, or Re-188.

33. The method of claim 32 wherein the radioactive metal is Sm-153.

34. The method of claim 32, wherein the radioactive metal is Ho-166.

* * * * *